(12) United States Patent
Neubardt

(10) Patent No.: US 9,833,332 B2
(45) Date of Patent: Dec. 5, 2017

(54) HARVESTING BONE GRAFT MATERIAL FOR USE IN SPINAL AND OTHER BONE FUSION SURGERIES

(71) Applicant: Seth L Neubardt, Mamaroneck, NY (US)

(72) Inventor: Seth L Neubardt, Mamaroneck, NY (US)

( * ) Notice: Subject to any disclaimer, the term of this patent is extended or adjusted under 35 U.S.C. 154(b) by 430 days.

(21) Appl. No.: 14/524,044

(22) Filed: Oct. 27, 2014

(65) Prior Publication Data

US 2016/0113779 A1    Apr. 28, 2016

(51) Int. Cl.
*A61B 17/16*   (2006.01)
*A61F 2/44*    (2006.01)
*A61B 17/32*   (2006.01)

(52) U.S. Cl.
CPC ........ *A61F 2/4455* (2013.01); *A61B 17/1635* (2013.01); *A61B 17/1671* (2013.01); *A61B 17/320068* (2013.01); *A61B 2017/320072* (2013.01)

(58) Field of Classification Search
CPC .................. A61B 17/1635; A61B 17/1671
See application file for complete search history.

(56) References Cited

U.S. PATENT DOCUMENTS

| | | | |
|---|---|---|---|
| 7,201,775 B2 | 4/2007 | Gorensek et al. | |
| 7,618,423 B1 | 11/2009 | Valentine et al. | |
| 8,328,870 B2 | 12/2012 | Patel et al. | |
| 8,343,178 B2 | 1/2013 | Novak et al. | |
| 8,353,912 B2 | 1/2013 | Darian et al. | |
| 8,425,610 B2 | 4/2013 | Guyer et al. | |
| 2004/0230305 A1* | 11/2004 | Gorensek | A61F 2/446 623/17.11 |
| 2006/0129243 A1 | 6/2006 | Wong et al. | |
| 2011/0035007 A1* | 2/2011 | Patel | A61F 2/4465 623/17.11 |
| 2012/0130380 A1 | 5/2012 | Babaev | |
| 2014/0058394 A1* | 2/2014 | Siegal | A61B 17/1671 606/80 |

(Continued)

OTHER PUBLICATIONS

Alphatec Spine, Inc., Solus(R) Anterior Lumbar Interbody Fusion, online advertisement (undated).

(Continued)

*Primary Examiner* — Samuel Hanna
(74) *Attorney, Agent, or Firm* — Leo Zucker

(57) ABSTRACT

A technique for harvesting bone graft material for spinal and other fusion surgeries. In the disclosed embodiment, a bone cutting blade is placed in a disc space between two vertebrae to be fused. The blade cuts into the vertebrae and forms solid segments of autologous bone inside each vertebra. Each bone segment is urged out of its associated vertebra until a first portion of the segment enters the opposite vertebra, an intermediate portion spans the disc space, and a second portion remains in the associated vertebra. Each segment thus forms a strut graft to promote a healthy and permanent fusion. In another embodiment, a wire is placed in the disc space and rotated to cut grooves in the vertebrae, causing a slurry of morselized cortical and cancellous bone to ooze into a cage that is placed in the disc space. The slurry heals to fuse the vertebrae solidly and permanently.

6 Claims, 8 Drawing Sheets

(56) References Cited

U.S. PATENT DOCUMENTS

2014/0163573 A1   6/2014   Neubardt

OTHER PUBLICATIONS

Biomet, Inc., C-Thru(tm) Anterior Spinal System, online advertisement (2014).
Biomet, Inc., Solitaire(tm)—C Anterior Spacer System, online advertisement (2014).
[cage brochures].

* cited by examiner

HARVESTING BONE GRAFT MATERIAL FOR USE IN SPINAL AND OTHER BONE FUSION SURGERIES

BACKGROUND OF THE INVENTION

Field of the Invention

The present invention relates to a procedure and system for harvesting bone graft material for use in skeletal bone fusion surgery, particularly in fusions of the spinal vertebrae.

Discussion of the Known Art

An object of spinal fusion surgery is to join adjacent vertebrae at an affected level of a patient's spine by inducing growth of solid bone tissue in the intervertebral disc space. The grown bone tissue acts to fuse the vertebrae together solidly and permanently. This procedure has long been known to reduce or eliminate severe back pain suffered by a patient when he or she assumes postures that cause the vertebrae at the affected level to move relative to one another in a certain manner.

See, e.g., my pending U.S. patent application Ser. No. 14/180,495 filed Feb. 14, 2014, titled Determining and Placing Spinal Implants or Prostheses, published as US 2014/0163573 (Jun. 12, 2014), and incorporated fully by reference.

In a typical fusion procedure, the disc space is cleaned and bone, or a bone-like graft material, is deposited in the space to promote the growth of bone tissue between the vertebrae and produce a healthy fusion. Among the available graft materials, bone graft harvested directly from the patient's own bone tissue ("autograft") or from a donor, ceramics, bone morphogenic proteins, and/or stem cell based grafts are commonly used as bone growth stimulants. Of these, autograft obtained from the patient's iliac crest or pelvic area is known to work best to promote a successful fusion.

Using the patient's own bone tissue for graft material works well to form a confluence of the material with the vertebral bones to be fused. It is also known that (a) the more autograft material used, the greater the likelihood of achieving a successful fusion, and (b) a solid piece of autograft material works better than smaller chips to promote fusion. Basic principles of orthopaedic surgery suggest an optimum fusion will occur when a solid bone piece is inserted to span the entire intervertebral disc space, and when opposite ends of the piece enter or penetrate the end plates of the two vertebrae that face the disc space.

U.S. Pat. No. 7,201,775 (Apr. 10, 2007) discloses a procedure that calls for implanting a hollow cylindrical stabilizing device (see FIGS. 7 & 8 of the patent) between the end plates of two vertebrae to be fused, and rotating the device so that it gouges and shears off portions of the end plates, which portions are then forced inside of the device. The device has openings so that when oriented as in FIG. 11C of the patent, the bone portions inside the device are exposed to the vertebrae through the openings to promote a fusion, according to the patent. The procedure runs a risk of crushing the end plates and destroying the integrity of the remaining vertebral bone, however. That is, one or both vertebrae can become prone to fracture and compress into the spinal canal. Further, the device does not translocate or displace an intact piece of bone directly from one vertebra so as to enter the body of the other vertebra.

U.S. Pat. No. 8,328,870 (Dec. 11, 2012) describes an interbody fixation system including a cage having blades mounted inside the cage. When the blades are turned not more than about 45 degrees as shown in FIGS. 2 and 6C of the patent, the blades bite into the end plates of the opposed vertebrae and fix the position of the cage on and between the end plates, according to the patent. See also, U.S. Pat. No. 7,618,423 (Nov. 17, 2009) which relates to a system for performing spinal fusion including a graft holder assembly, a locking assembly, and a pair of bone graft implants that are introduced into a disc space to effect fusion; U.S. Pat. No. 8,353,912 (Jan. 15, 2013) disclosing an ultrasonic cleaning device for leveling the surfaces of the vertebral end plates after the disc space is cleaned and before graft material is deposited in the space, and U.S. Pat. No. 8,343,178 (Jan. 1, 2013) describing an ultrasonic saw blade for cutting hard bone without damaging adjacent soft tissue. All of the foregoing U.S. patents are fully incorporated by reference.

Notwithstanding known meticulous procedures to obtain and use autograft material from a patient during a surgical procedure, there is no guarantee that a reliable and strong fusion will ultimately result, and that a so-called "non-union" will be avoided. A need therefore exists for a system and procedure for obtaining and depositing autograft material between two vertebrae to be fused so that the material spans the intervertebral disc space, enters the vertebral bodies, and grows rapidly to produce a healthy, strong, and permanent fusion.

SUMMARY OF THE INVENTION

According to one aspect of the invention, a procedure for harvesting bone graft material for use in a skeletal bone fusion surgery, includes inserting a cutting blade to a certain position inside a space between first and second bones to be fused, and rotating the blade so that it cuts into both of the bones and forms solid bone segments within each of the first and the second bones. Each bone segment is displaced to a position at which a first end portion of the segment is located in the first bone, an intermediate portion of the segment spans the space between the two bones, and a second end portion of the segment is located in the second bone. The bone segment thus forms a strut graft that acts as a pathway for bone growth to fuse the first and the second bones with one another.

According to another aspect of the invention, a procedure for harvesting bone graft material for use in a skeletal bone fusion surgery, includes inserting a cutting blade to a certain position inside a space between first and second bones to be fused, and rotating the blade so that it cuts multiple grooves into the bones, and produces a slurry of morselized cortical and cancellous bone that oozes from the two bones. The slurry is confined in the region of the bones so that upon healing, the slurry becomes solid bone that fuses the first and the second bones with one another.

For a better understanding of the invention, reference is made to the following description taken in conjunction with the accompanying drawing and the appended claims.

BRIEF DESCRIPTION OF THE DRAWING FIGURES

DETAILED DESCRIPTION OF THE INVENTION

The present invention resides in harvesting bone graft material directly from bones to be fused in a surgical procedure on a patient, in situ. In the illustrated embodiment, the procedure is a spinal fusion wherein the bones to be fused are spinal vertebrae, and the harvested material spans the disc space between the vertebrae and enters the vertebral bodies. As a result, the graft material grows quickly to obtain a healthy, solid, and permanent fusion. While the invention is illustrated and described below as applied to a spinal fusion, persons skilled in the art will recognize that the invention can be applied in other bone fusion surgeries, for example, fusions of the ankle.

Figure 1:
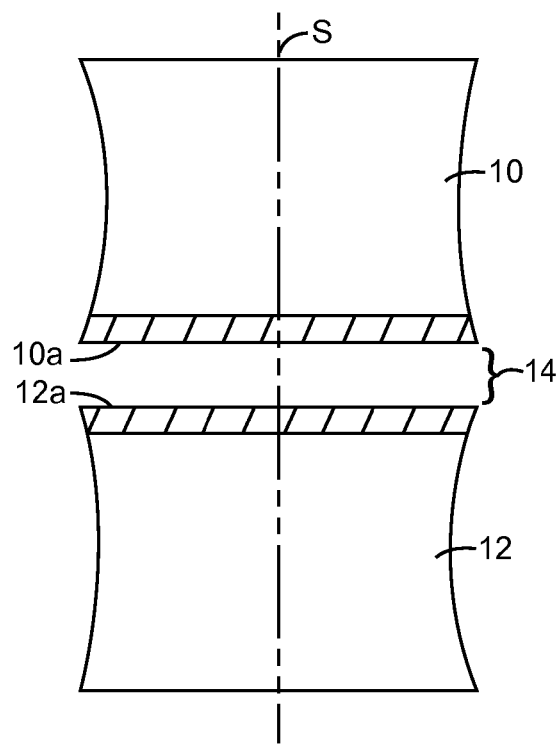
FIG. 1 is a diagram of two adjacent spinal vertebrae to be fused with one another according to a first embodiment of the invention.

FIG. 1 is a diagram showing two adjacent vertebrae 10, 12 in a patient's spine. The spine has an axis S, and the two vertebrae 10, 12 are separated by a disc space 14. The vertebrae have end plates 10a, 12a that face one another across the disc space 14.

Figure 3:
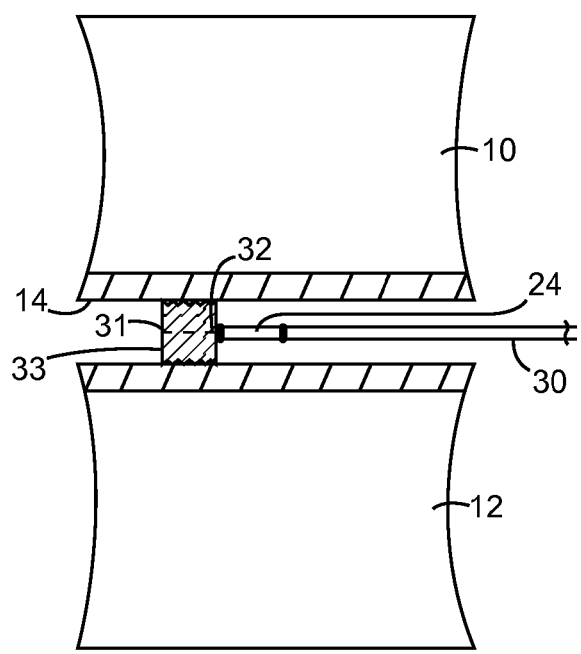
FIG. 3 is a diagram of the tool shaft in FIG. 2 inserted inside a disc space between the vertebrae in FIG. 1, and a cage to which the shaft is pivoted for rotation with the cutting blade.
Figure 2:
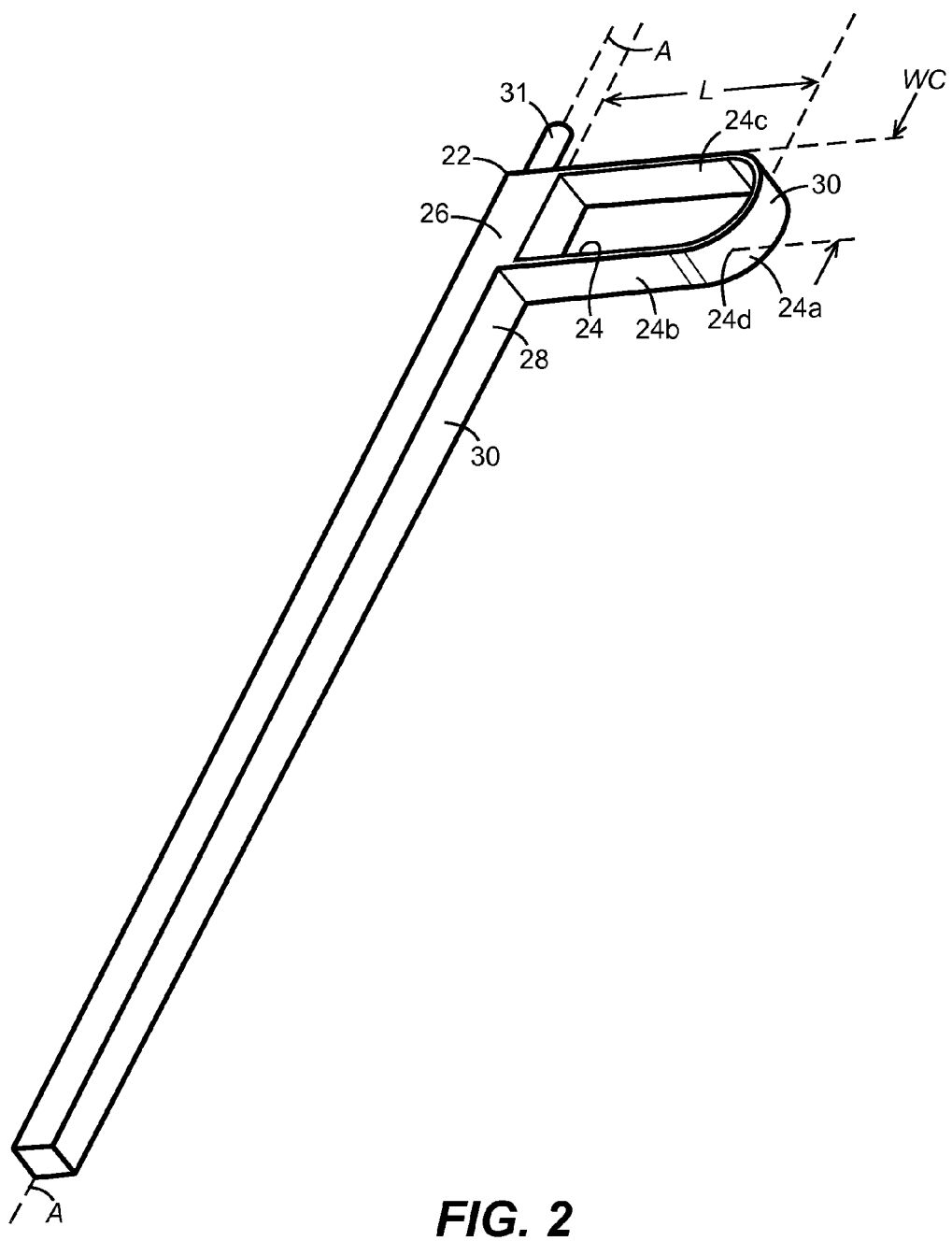
FIG. 2 shows a tool shaft with an associated cutting blade at a distal end of the shaft, according to the invention.

In one embodiment of the invention, shown in FIGS. 2 to 9, a bone cutter 20 has a base 22 and a generally U-shaped, two-dimensional ultrasonic cutting blade 24. The blade 24 has a cutting edge 24a formed along legs 24b, 24c, and a closed end 24d of the "U" shaped blade 24. As shown in FIG. 2, the blade legs 24b, 24c are spaced apart by width WC, and the closed end 24d of the blade is at a length L from the bone cutter base 22. The base 22 is fixed at 26 to a distal end 28 of a tool shaft 30 having an axis A, and the tool shaft 30 has an axial pivot 31 extending from the distal end 28. As seen in FIG. 3, the pivot 31 at the distal end 28 of the shaft 30 is received in a corresponding pivot opening 32 formed in a spacer or cage 33 after the cage is placed in the disc space 14 between the vertebrae 10, 12.

The cage 33 can be formed of a surgical metal, polymer, ceramic, or composites thereof. In addition to providing a common axial pivot or anchor point for the tool shaft 30 and other instrumentation to be aligned between the end plates 10a, 12a of the vertebrae, the cage 33 supports the vertebral bones 10, 12 above and below the disc space 14 to prevent subsidence of graft bone segments obtained as described below. The cage 33 also enhances the stability of the entire construct to ensure a successful fusion.

If surgery is performed using a posterior approach, the cage 33 enters the disc space 14 from the posterior side, and should be urged anteriorly as far as possible to lodge against the disc annulus while the vertebral bones 10, 12 compress against the cage. To provide an effective anchor point for the pivot 31 on the tool shaft, the cage 33 should be relatively large and have a curvilinear shape to conform with the anterior disc space occupied by the cage 33. Cages usually have an aperture to allow bone graft material to be deposited inside them, and for the material to contact vertebrae above and below the cage so that a solid bond between the vertebrae will grow through the cage itself.

Because, as explained below, the inventive procedure obtains bone graft material directly from the vertebrae to be fused rather than an outside source, it is therefore not critical for the cage 33 to act primarily as a fusion device. The cage 33 can work mainly as a fixation device that connects to the vertebral bones 10, 12 above and below the cage. An example of a suitable cage that also acts as a fixation device is available from Biomet, Inc., as the C-THRU™ Anterior Spinal System. The Biomet cage has with a large chamber that opens at the superior and inferior (top and bottom) ends of the cage for in which graft material can be packed. Although the cage 33 as shown in FIG. 3 is not centered directly beneath the portions of the vertebrae 10, 12 to be cut, it may be desirable to use a cage such as the Biomet with a chamber that opens at both ends, and to form an opening in a side of the cage to allow the cutting blade 24 at the distal end of the tool shaft 30 to pass into the chamber. The cage 33 can then be centered directly beneath the facing surfaces on the bones 10, 12 to be cut. (See FIG. 11, cage 100).

Figure 4:
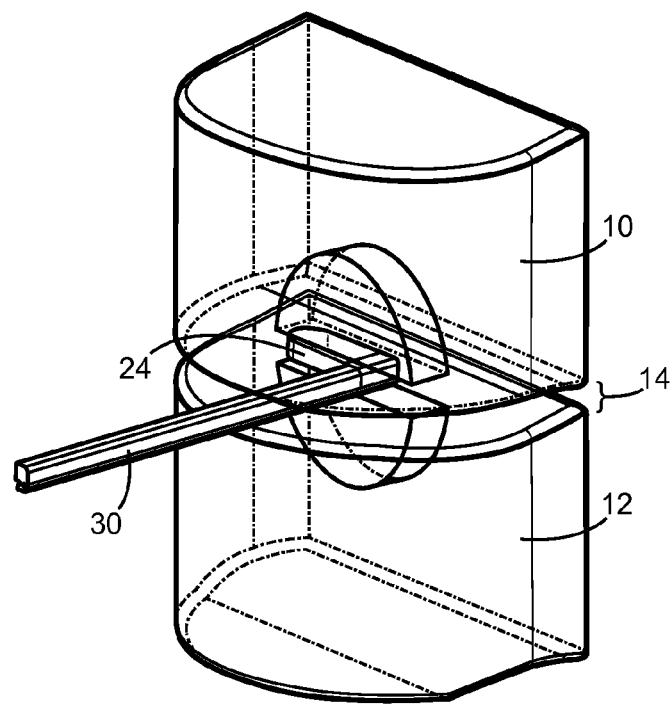
FIG. 4 is an enlarged, isometric view of the tool shaft and cutting blade inserted in the disc space as in FIG. 3.
Figure 5:
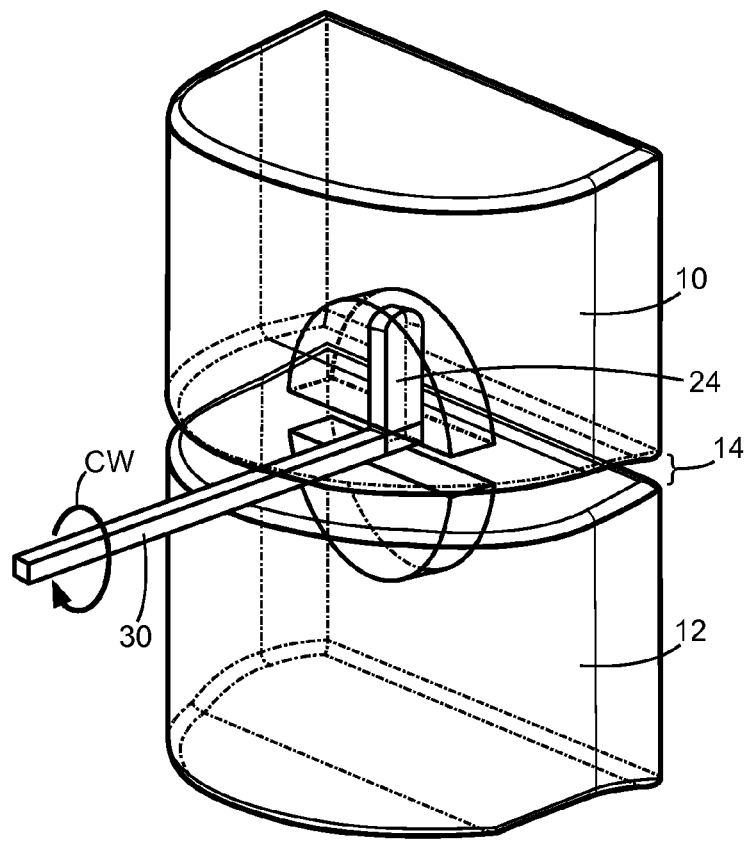
FIG. 5 is a view similar to FIG. 4, showing the cutting blade turned 90 degrees from the position in FIG. 4 by the tool shaft.

As seen in FIG. 2, the "U" shape cutting blade 24 extends radially outward from its base 22 at the distal end 28 of the tool shaft 30. The legs 24b, 24c and the closed end 24d of the blade 24 extend in a plane that coincides with the shaft axis A. The bone cutter 20 including the cutting blade 24 is dimensioned and configured to be inserted with the tool shaft 30 to a desired position in the disc space 14, with the plane of the cutting blade 24 held generally parallel to the end plates 10a, 12a of the vertebrae to be fused, as shown in FIG. 4. The cutting edge 24a of the blade 24 is activated, for example, by a conventional ultrasonic driver coupled to the tool shaft 30 in a known manner. Ultrasonically energized bone cutting blades are known generally, and persons skilled in the art can construct and use the blade 24 as described herein. See, e.g., the website at www.misonix.com.

Figure 6:
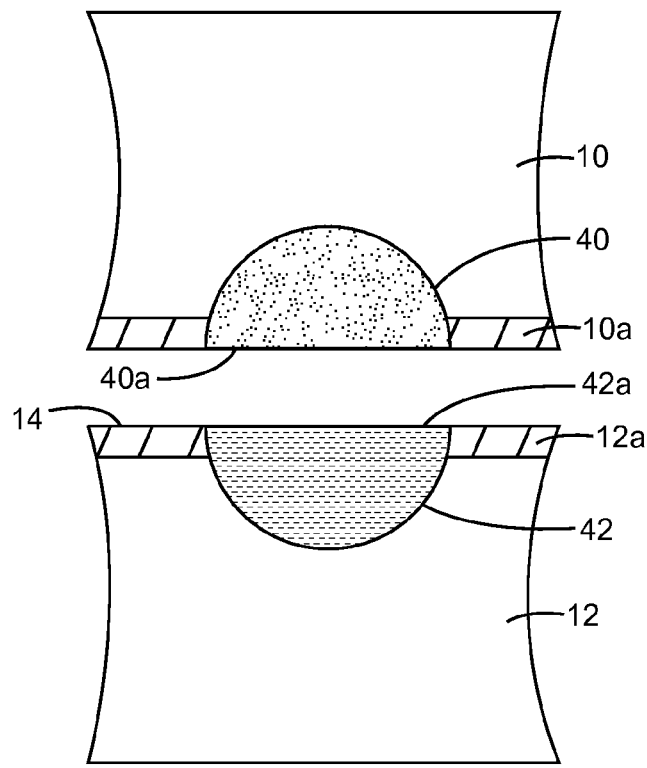
FIG. 6 illustrates two semicircular bone segments formed inside the vertebrae after the cutting blade is rotated over 360 degrees by the tool shaft.
Figure 10:
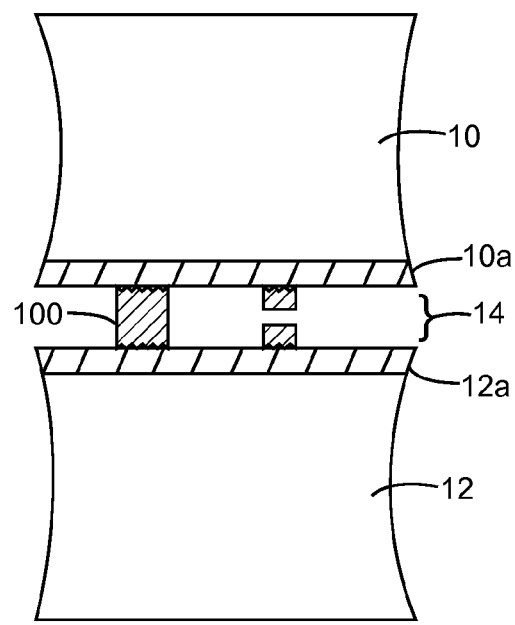
FIG. 10 shows the vertebrae in FIG. 1 to be fused with one another according to a second embodiment of the invention, including a cage placed in the disk space.

In the inventive procedure, the tool shaft 30 is rotated about the shaft axis A by, e.g., a removable or cannulated handle (not shown in the drawing) having an axial thru passage that is keyed to a cross sectional profile of the shaft, or by a flexible motor drive, so that the cutting edge 24a of the blade 24 is urged over a circular path that cuts into the vertebral end plates and adjacent regions inside the vertebrae 10, 12. See FIG. 5. As a result, as depicted in FIG. 6, the cutting blade 24 forms two solid, semicircular bone segments 40, 42 in the vertebral bodies 10, 12 wherein the radius of each segment 40, 42 corresponds to the length L of the blade 24 from the shaft axis A, and the thickness of each segment corresponds to the spacing WC between the blade legs 24b, 24c.

The bone segments 40, 42 are comprised of autologous graft material that is then used to form strut grafts between the same vertebrae 10, 12 from which the grafts are formed. Note that in FIG. 6 that flat surfaces 40a, 42a of the segments are exposed to face one another across the intervertebral disc space 14. While the tool shaft 30 may be withdrawn with the cutting blade 24 from the disc space 14 at this time, it is preferred that the shaft and the blade remain in place as noted below.

Figure 7:
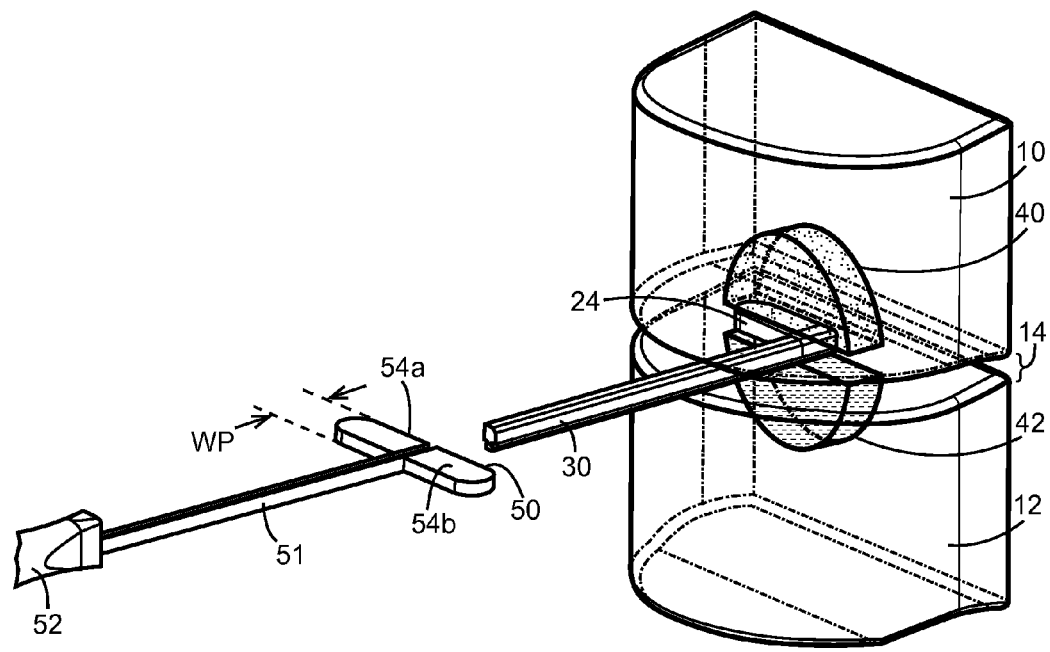
FIG. 7 is an isometric view of a pusher or paddle fixed at a distal end of a cannulated shaft that slides over the tool shaft.
Figure 8:
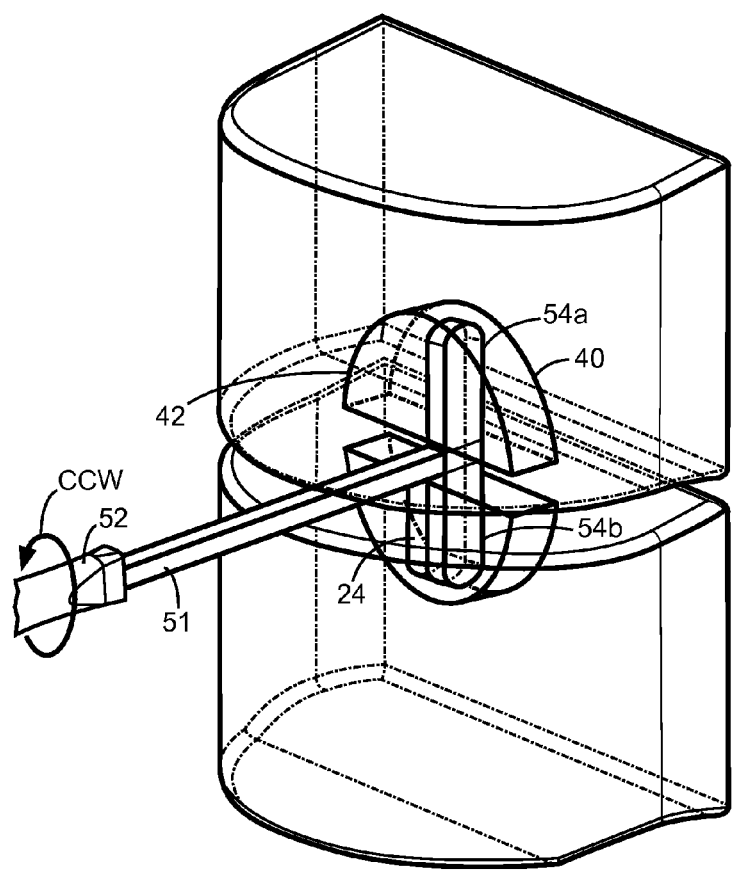
FIG. 8 is a view similar to FIG. 7, showing paddle inserted in the disc space and turned 90 degrees from the angular position of the paddle in FIG. 7 by the cannulated shaft.
Figure 9:
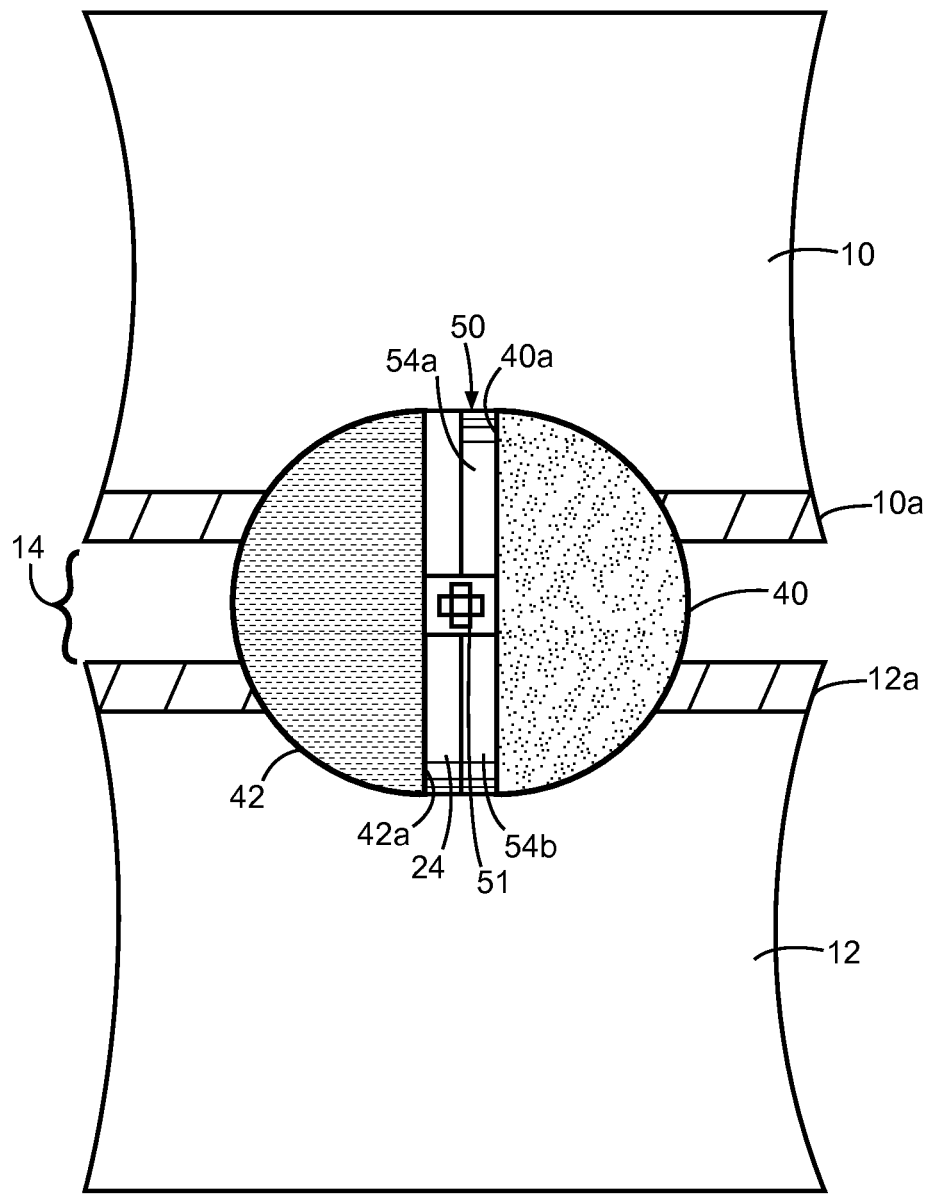
FIG. 9 illustrates the bone segments in FIG. 6 forming two strut grafts between the vertebrae when the paddle is in the position shown in FIG. 8, according to the invention.

After removing a handle or other drive from the tool shaft 30, and as shown in FIGS. 7 to 9, an elongated pusher or paddle 50 is inserted into the disc space 14 until the paddle overlies the cutting blade 24 and extends substantially entirely over the exposed flat surfaces of the vertebral bone segments 40, 42. In the disclosed embodiment, the paddle 50 is formed at a distal end of a cannulated shaft 51 whose axial passage is keyed to the cross section of the tool shaft 30. The cannulated shaft 51 is slid over the tool shaft 30, a handle 52 is provided at the proximal end of the shaft 51, and the paddle 50 is inserted inside the disc space 14. Using the handle 52, the paddle 50 is rotated (together with the blade 24 if left in place) through the same circular path initially cut by the blade 24 through the vertebrae 10, 12.

If the cage 33 is of such size that it encompasses areas of the vertebral end plates 10a, 12a that will be cut by the blade 24, the blade 24 and the paddle 50 must then be able to be inserted and operate within the perimeter of the cage. In such a case, the cage may be formed with a through passage between its anterior and posterior facing side walls. The dimensions of the passage must be such as to allow of the tool shaft 30 with the bone cutting blade 24, the cannulated shaft 51 with the paddle 50, and any other needed instrumentation to pass and operate inside the cage 70 when performing the inventive fusion procedure.

In the illustrated embodiment, the paddle 50 has two "U" shaped arms 54a, 54b that extend outward and 180 degrees apart from one another as shown in FIGS. 7 to 9. Each paddle arm 54a, 54b has a width WP that does not exceed the width WC of the bone cutter blade 24. Likewise, the length of each paddle arm 50a, 50b does not exceed about one-half the length of either of the exposed surfaces 40a or 42a of the bone segments 40, 42 facing the disc space 14. The entire paddle 50 may also be formed from one or more balloons which, when inflated, take the form of a rigid pusher or paddle device.

When the paddle 50 is inserted in the disk space 14, the paddle arms 54a, 54b are generally parallel to and overlie the exposed surfaces 40a, 40b of the bone segments 40, 42 formed by the blade 24. The cannulated shaft 51 is turned about its axis A until each paddle arm 54a, 54b abuts the exposed surface of one of the bone segments, and the shaft 51 is turned about 90 degrees farther so that the paddle arms 54a, 54b urge the bone segments 40, 42 to rotate in unison within their associated vertebra until, as shown in FIG. 9, (i) a leading portion of each segment 40, 42 enters the vertebra opposite the vertebra in which the segment was formed, (ii) a central portion of each segment spans the disc space 14 entirely, and (iii) a trailing portion of each segment remains inside the vertebra in which it was formed.

When displaced as described above and shown in FIG. 9, each one of the bone segments 40, 42 forms a vertical bridge strut graft that completely spans the disc space 14 and also enters the vertebrae 10, 12 above and below the space. Each strut graft acts as a pathway for bone growth and promotes a healthy fusion of the vertebrae. The tool shaft 30 is then withdrawn from the cage 33 inside the disc space 14, and the paddle 50 and the blade 24 can remain in a vertical orientation between the displaced bone segments 40, 42 without affecting the quality of the ensuing fusion.

After the cutting blade 24 cuts through the vertebrae 10, 12, and especially after the bone segments 40, 42 are rotated, there will likely be a massive release of blood since the bone is very vascular. Accordingly, in addition to inserting and using a cage such as the mentioned Biomet device for the cage 33 in the disk space 14, a system should be in place to extinguish such hemorraging. One approach is to use a coagulating agent such as, for example, the Surgiflo® Hemostatic Matrix available from Ethicon US, LLC, and injecting the agent through an applicator tube into a port formed on the cage 33. Also, with much bleeding, there may be a need to seal the disc space 14 so that the coagulating agent stays within the disc space. That is, the disc space 14 may need to be capped or sealed closed to confine the blood, the coagulating agent, and the graft bone segments within the disc space. With the coagulating agent injected into the closed disc space which provides a pressurized environment, bleeding will stop.

Further, the cage may also have ports so situated that the coagulating agent makes a seal between the upper and the lower surfaces of the cage, and the adjacent vertebral bone. This would prevent bloody fluid from escaping above and below the cage through small gaps.

When the paddle 50 is rotated, it is urged against the exposed surfaces 40a, 42a of the bone graft segments 40, 42 after the segments were cut and formed by the blade 24. The paddle 50 does not occupy any space in which new bone graft is being deposited. That is, the paddle 50 is not embedded in any new bone growth, but remains in a final vertical position with the bone segments 40, 42 at each side, and with the vertebral bones 10, 12 above and below the paddle.

As the bones 10, 12 heal and the graft bone segments 40, 42 grow, the paddle 50 becomes firmly anchored inside the vertebrae 10, 12 and thereby adds stability to the overall construct by pinning the vertebrae together. To that end, the paddle 50 may be constructed, for example, with extensible pins to engage the exposed surfaces 40a, 42a of the bone segments and/or the vertebrae 10, 12 above and below the paddle 50. Such engagement would stabilize the entire construct and ensure that the paddle 50 and the graft bone segments 40, 42 do not migrate. Together with the cage 33, the paddle 50 also prevents subsidence with collapse of the disc height.

It is also possible for the paddle 50 to be constructed of balloons so that, if desired after inflation and use, the paddle can be deflated and easily removed after it is rotated to a vertical position with the bone segments 40, 42 at either side. In such an embodiment, however, any additional fixation that would otherwise result from using a more solid form of the paddle 50 will not be realized unless the balloons are later filled with a material such as, e.g., methyl methacrylate that hardens in place.

The paddle 50 may also be constructed in a known manner so that the two arms 54a, 54b of the paddle overlie one another at one side of the cannulated shaft as the paddle is being inserted inside the disc space 14. When between the vertebrae 10, 12, one of the arms may then be displaced to the opposite side of the shaft so that the paddle extends fully across the exposed surfaces 40a, 42a of the bone segments above and below the paddle.

It is preferable that the solid bone cutting blade 24 remain in situ, and no attempt made to withdraw the blade from between the bone segments 40, 42 after the blade forms the segments and the paddle 50 is inserted into the disk space 14. This ensures the paddle 50 will displace the bone segments 40, 42 over the identical path cut by the blade 24 through the vertebrae 10, 12, since a variance of even one millimeter to either side of the path can cause the paddle 50 to lock against solid uncut vertebral bone and prevent the paddle from displacing the segments 40, 42 fully to the positions in FIG. 9. If the cage 33 provides enough precision with respect to the position of the blade 24 and the paddle 50 during use, however, it may be possible to remove the cutting blade 24 prior to inserting and using the paddle 50.

The above procedure has the following features:

1. The bone cutting blade 24 can be activated ultrasonically to make the vertebral cuts safely and precisely;

2. The cutting blade 24 and the paddle 50 can be made small enough to be inserted into the intervertebral disc space 14 during a minimally invasive surgical procedure; and 3. In addition to adding stability to the construct, the cage 70 provides a common pivot point for the rotation of the bone cutting blade 24 and the paddle 50, to ensure the bone segments 40, 42 are displaced smoothly and accurately by the paddle after being formed by the blade.

Another embodiment of the inventive system and procedure is illustrated in FIGS. 10 to 14. Instead of cutting and forming the solid autograft segments 40, 42 and displacing them as described above, a bone cutting instrument having a straight rather than a two-dimensional or "U" shaped cutting edge like the blade 24 is inserted into the disc space 14 instead. The instrument is operated to strike the vertebral bones 10, 12 and groove them in such a way that a slurry of morselized cortical and cancellous bone rich in osteogenic cells and blood oozes from the vertebrae. By confining the slurry within the disc space 14, the slurry also remains present in the vertebrae 10, 12, and thus forms a solid bony fusion of the two vertebrae.

A cage 100 is set in the disc space between the vertebrae 10, 12. See FIG. 10. The cage 100 may be similar to the earlier mentioned Biomet C-THRU Anterior Spinal System device, or equivalent. In addition, the cage 100 should have sufficient size and volume to contain and confine the slurry to be produced from the vertebrae as detailed below, and be constructed so its edges seal any gaps between the cage and either bone 10, 12. As described above with respect to the embodiment of FIGS. 1 to 9, such sealing prevents liquid graft material from migrating outside the internal chamber of the cage 100 and the intervertebral disc space. For example, a seal can be formed by constructing the cage 100 with internal and/or external channels that guide a sealing agent around the circumference of the superior and inferior edges of the cage 100, and the agent can be injected into the cage during the procedure. The mentioned Surgiflo® Hemostatic Matrix is an example of such a sealing agent.

Figure 11:
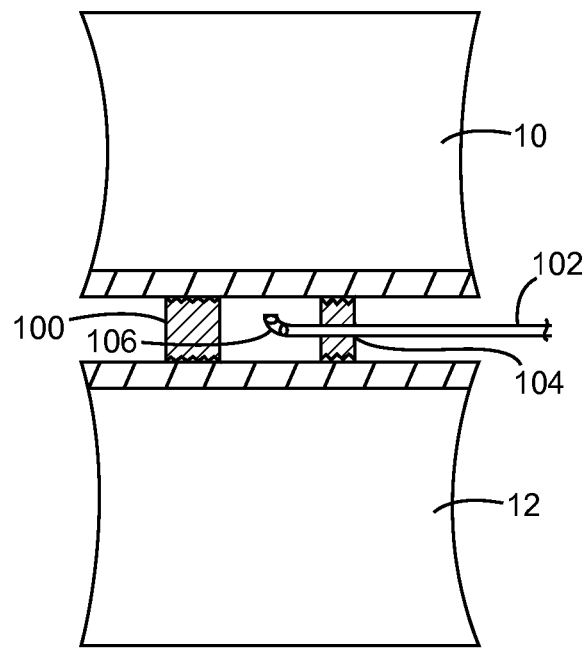
FIG. 11 shows a distal end of a cannula inserted in the disc space through an opening in a side wall of the cage in FIG. 10.
Figure 12:
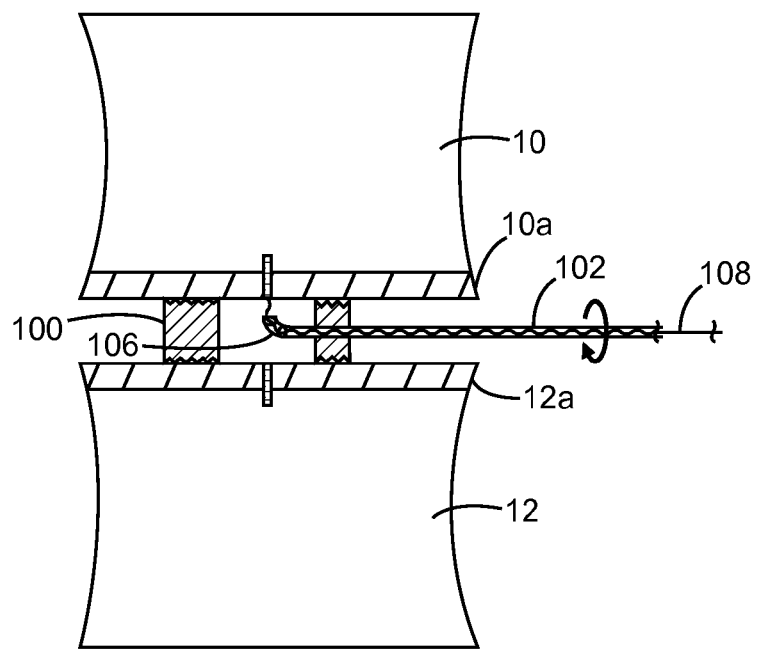
FIG. 12 shows a cutting tip of a flexible wire inserted through the cannula and into the disk space, with the tip angled toward one of the vertebrae.
Figure 13:
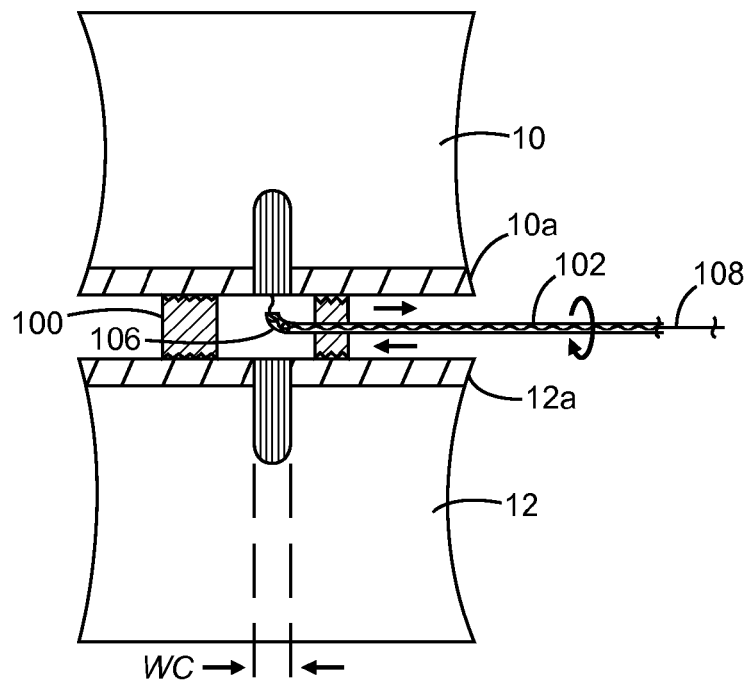
FIG. 13 shows the tip of the wire cutting multiple grooves in the vertebrae when the tip is rotated and displaced laterally in the disc space by the cannula.

As seen in FIGS. 11 to 13, a cannula 102 is inserted through an opening 104 in the wall of the cage 100, and the cannula 102 has a distal tip 106 that is angled toward the vertebrae above and below the perimeter of the cage. A flexible, sharp tipped wire 108 is inserted through the cannula 102, past the distal tip 106 of the cannula, and against the end plate 10*a* or 12*a* of a confronting vertebra. A motor or other drive mechanism coupled to a proximal end of the cannula 102 spins the cannula so that the sharp tip of the wire 108 cuts into the end plates 10*a*, 12*a* of both vertebrae 10, 12.

The wire 108 is pushed farther into the cannula 102 so that the wire tip cuts a groove completely through the end plates and adjacent regions of the vertebrae 10, 12, as seen in FIG. 12. The position of the wire 108 at the tip 106 of the cannula is adjusted and the cannula 102 is moved axially in anterior and posterior directions so that the combined width WC of all the vertebral cuts is increased as desired. See FIG. 13. The cannula 102 and wire 108 are then withdrawn from inside the cage 100 and the disc space.

Figure 14:
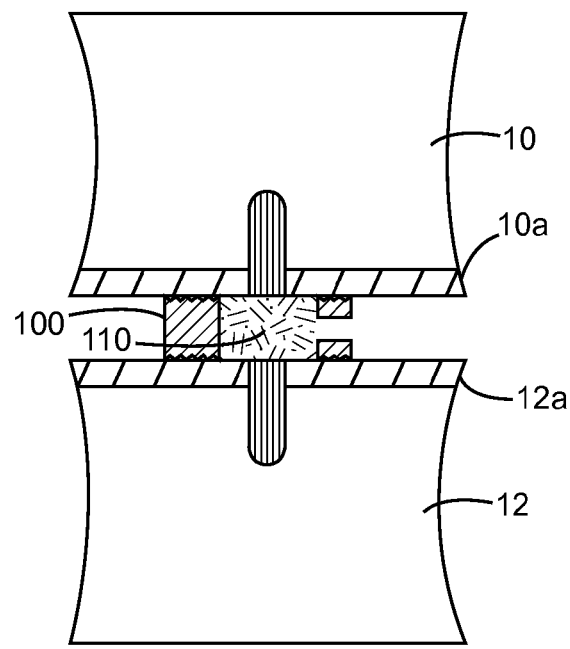
FIG. 14 shows a bony slurry produced by the cut vertebrae and confined by the cage so as to fuse the vertebrae with one another, according to the invention.

As a result and as shown in FIG. 14, all of the bony slurry 110 obtained from the cut vertebrae will either be contained inside the cage 100 in the disc space, or within the vertebrae 10, 12 in the region of the grooved cuts. Upon healing, the slurry forms a solid bony fusion of the vertebrae. If needed, a second cage or other device can be provided to cap or otherwise seal the cage 100 and the disc space to ensure the slurry stays so confined before healing.

While the foregoing represents preferred embodiments of the invention, it will be understood by those skilled in the art that various modifications, adaptations, and additions may be made without departing from the spirit and scope of the invention. For example, while the invention is described herein as applied to a spinal fusion, the invention may be adapted for other bone fusion procedures as well, for example, ankle bone fusions. Accordingly, invention includes all such modifications, adaptations, and additions that are within the scope of the following claims.

I claim:

1. A procedure for harvesting bone graft material for use in skeletal bone fusion surgery, comprising:

placing a cage to a certain position inside a space between first and second bones to fuse the first and second bones, and expose portions of the bones to an inside region of the cage defining a cavity;

inserting a cannula, having a longitudinal axis and an axial passage extending therethrough, through an opening in a side wall of the cage, positioning a distal tip of the cannula within the inside region of the cage, and angling the distal tip of the cannula toward the exposed portions of the first and second bones to be fused;

inserting a flexible wire having a cutting tip through the axial passage and past the distal tip of the cannula to enter the inside region of the cage at a position at which the cutting tip of the wire faces the exposed portions of the first and the second bones;

rotating the cutting tip of the wire and cutting multiple grooves into the exposed portions of the first and the second bones until a slurry of morselized cortical and cancellous bone oozes from the exposed portions of the first and second bones into the inside region of the cage, by rotating the cannula about the longitudinal axis while pushing the wire into the axial passage of the cannula so that the cutting tip of the wire is against the exposed portions of the first and second bones;

confining the slurry within the inside region of the cage;

withdrawing the cannula and the flexible wire from the inside region of the cage after the bony slurry oozes from the cut bones; and leaving the cage containing the slurry in the space between the first and second bones until the slurry forms a solid bone in the cavity of the cage that fuses the first and the second bones with one another when the bones heal and the slurry grows.

2. The bone graft material harvesting procedure of claim 1, wherein the first and the second bones are first and second vertebrae in a patient's spine, and the cutting tip of the wire is inserted through the passage in the cannula to a position inside of a disc space between the first and the second vertebrae.

3. The bone graft material harvesting procedure of claim 1, including sealing the cage for preventing the confined slurry from escaping the inside region of the cage.

4. The bone graft material harvesting procedure of claim 1, including adjusting the position of the cutting tip of the wire at the distal tip of the cannula and moving the cannula in anterior and posterior directions along the longitudinal axis, thereby increasing a combined width of the multiple grooves cut into the exposed portions of the first and the second bones by the cutting tip of the wire as desired.

5. The procedure of claim 3, including forming channels in the cage for guiding a sealing agent around the circumference of superior and inferior edges of the cage.

6. The procedure of claim 5, including injecting the sealing agent into the cage during the procedure.

\* \* \* \* \*